US006684683B2

(12) United States Patent
Potyrailo et al.

(10) Patent No.: US 6,684,683 B2
(45) Date of Patent: Feb. 3, 2004

(54) METHOD AND APPARATUS FOR CHARACTERIZING THE BARRIER PROPERTIES OF MEMBERS OF COMBINATORIAL LIBRARIES

(75) Inventors: Radislav Alexandrovich Potyrailo, Niskayuna, NY (US); Michael Jarlath Brennan, Burnt Hills, NY (US)

(73) Assignee: General Electric Company, Niskayuna, NY (US)

( * ) Notice: Subject to any disclaimer, the term of this patent is extended or adjusted under 35 U.S.C. 154(b) by 115 days.

(21) Appl. No.: 10/083,436

(22) Filed: Feb. 27, 2002

(65) Prior Publication Data

US 2003/0160194 A1 Aug. 28, 2003

(51) Int. Cl.[7] ............................................. G01N 29/02
(52) U.S. Cl. .................... 73/24.06; 73/31.06; 73/30.04; 73/32 A; 73/54.24; 73/54.38; 73/54.41; 73/61.49; 73/61.75; 73/61.79; 422/68.1
(58) Field of Search ................. 73/24.01, 24.03, 73/24.04, 24.05, 24.06, 30.01, 30.04, 31.01, 31.02, 31.03, 31.05, 31.06, 32 R, 32 A, 53.01, 54.01, 54.02, 54.23, 54.24, 54.25, 54.26, 54.38, 54.41, 61.45, 61.49, 61.75, 61.79, 579; 310/360, 316, 320; 422/68.1, 75, 98

(56) References Cited

U.S. PATENT DOCUMENTS

| | | | |
|---|---|---|---|
| 5,015,843 A | 5/1991 | Seitz et al. ............ 250/227.21 |
| 5,591,898 A | 1/1997 | Mayer .......................... 73/38 |
| 5,891,398 A | * 4/1999 | Lewis et al. ............. 422/82.02 |
| 5,985,356 A | * 11/1999 | Schultz et al. ................ 427/8 |
| 6,009,743 A | 1/2000 | Mayer .......................... 73/38 |
| 6,030,917 A | * 2/2000 | Weinberg et al. ........... 502/104 |
| 6,045,671 A | * 4/2000 | Wu et al. .............. 204/298.11 |
| 6,182,499 B1 | * 2/2001 | McFarland et al. ........ 73/24.06 |
| 6,321,588 B1 | * 11/2001 | Bowers et al. ............. 73/24.01 |

FOREIGN PATENT DOCUMENTS

WO    WO 98/15501    * 4/1998

OTHER PUBLICATIONS

Rharbi, Y,; Yekta, A.; Winnik, M. A. , A method for measuring oxygen diffusion and oxygen permeation in polymer films based on fluorescence quenching, *Anal. Chem.* 1999, 71, 5045–5053.

Ward, M.; Buttry, D. A., In situ interfacial mass detection with piezoelectric transducers, *Science* 1990, 249, 1000–1007.

(List continued on next page.)

*Primary Examiner*—Hezron Williams
*Assistant Examiner*—Rose M. Miller
(74) *Attorney, Agent, or Firm*—Andrew J. Caruso; Patrick K. Patnode

(57) ABSTRACT

A method and an apparatus for characterizing the barrier properties of an array of coatings. The method including providing a plurality of acoustic wave devices, wherein each of the plurality of acoustic wave devices comprises at least one surface, and providing a plurality of coating materials suitable for forming a plurality of coatings on the at least one surface of each of the plurality of acoustic wave devices. The method also including coating each of the plurality of acoustic wave devices with at least one of the plurality of coating materials to form a plurality of coated acoustic wave devices and measuring a predetermined output parameter of each of the plurality of coated acoustic wave devices. The method further including exposing the plurality of coated acoustic wave devices to an analyte vapor of a predetermined concentration, measuring the predetermined output parameter of each of the plurality of coated acoustic wave devices, and correlating a change in the predetermined output parameter of each of the plurality of coated acoustic wave devices to the barrier properties of each of the plurality of coatings.

41 Claims, 8 Drawing Sheets

OTHER PUBLICATIONS

Ballantine, D. S., Jr.; White, R. M.; Martin, S. J.; Ricco, A. J.; Frye, G. C.; Zellers, E. T.; Wohltjen, H. *Acoustic Wave Sensors: Theory, Design, and Physico–Chemical Applications*; Academic Press: San Diego, CA, 1997, pp 150–221.

Potyrailo, R. A.; May, R. J.; Sivavec, T. M.; Recognition and quantitation of closely related chlorinated organic vapors and with acoustic wave chemical sensor arrays, Proc. SPIE––Int. Soc. Opt. Eng., 3856(Internal Standardization and Calibration Architectures for Chemical Sensors) 80–87 (1999).

Potyrailo, R. A.; Sivavec, T. M.; Bracco, A. A., Field evaluation of acoustic wave chemical sensors for monitoring of organic solvents in groundwater, Proc. SPIE–Int. Soc. Opt. Eng., 3856(Internal Standardization and Calibration Architectures for Chemical Sensors) 140–147 (1999).

Ranucci, E.; Ferruti, P.; Opelli, P.; Ferrari, V.; Marioli, D.; Taroni, A., Poly(N–vinylpyrrolidone) as moisturesorbing material for relative humidity sensors, *Sens. Mater.* 1994, 5, 221–229.

Freud, M. S.; Lewis, N. S., A chemically diverse conducting polymer–based "electronic nose", *Proc. Natl. Acad. Sci. USA* 1995, 92, 2652–2656.

Woolfson, A. D., Moisture–activated, electrically conducting bioadhesive interfaces for biomedical sensor applications, *Analyst* 1996, 121, 711–714.

Vaid, T. P.; Burl, M. C.; Lewis, N.S., Comparison of the performance of different discriminant algorithms in analyte discrimination tasks using an array of carbon black–polymer composite vapor detectors, *Anal. Chem.* 2001, 73, 321–331/.

Matsuguchi, M.; Umeda, S.; Sadaoka, Y.; Sakai, Y., Characterization of polymers for a capacitive–type humidity sensor based on water sorption behavior, *Sens. Actuators B* 1998, 49, 179–185.

Gauglitz, G., Optical Sensor Array Based On Microtiterplate Dimensions, Mikrochim, Acta 131, 9–17 (1999).

Woolfson, D.A., Moisture–activated, Electrically Conducting Bioadhesive Interfaces for Biomedical Sensor Applications, Analyst, Jun. 1996, vol. 121 (711–714).

Hubert, T., Humidity–Sensing Materials, MRS Bulletin, Jun. 1999, vol. 24, No. 6, pp. 49–54.

Hinkers, J.; Hermes, T.; Sundermeier, C.; Borchardt, M.; Dumschat, C.; Bucher, S.; Buhner, M.; Cammann, K.; Knoll, M., An amperometric microsensor array with 1024 individually addressable elements for two–dimensional concentration mapping, Elsevier Scioence S.A. , Sensors and Actuators B 24–25 (1995) 300–303.

Brecht, A.; Burckardt, R.; Rickert, J.; Stemmler, I.; Schuetz, A.; Fischer, S.; Friedrich, T.; Gauglitz, G.; Goepel, W., Transducer–Based Approaches for Parallel Binding Assays in HTS, Journal of Biomolecular Screening, vol. 1, No. 4, 1996, pp. 191–201.

Ogura, K.; Shiigi, J.; Nakayama, M., A New Humidity Sensor Using the Composite Film Derived from Poly(o–phenylenediamine) and Poly(vinyl alcohol), J. Electrochem. Soc., vol. 43, No. 9, Sep. 1996, pp. 2925–2930.

Hoyt, A.E., Ricco, A.J.; Bartholomew, J.W.; Osbourn, G.C.; SAW Sensors for the Room–Temperature Measurement of CO2 and Relative Humidity, Analytical Chemistry, vol. 70, No. 10, May 15, 1998, pp. 2137–2145.

Penza, M.; Cassano, G., Relative humidity sensing by PVA–coated dual resonator SAW oscillator, Elsevier Science S.A., Sensors and Actuators B 68 (2000) 300–306.

* cited by examiner

METHOD AND APPARATUS FOR CHARACTERIZING THE BARRIER PROPERTIES OF MEMBERS OF COMBINATORIAL LIBRARIES

STATEMENT OF FEDERALLY SPONSORED RESEARCH AND DEVELOPMENT

The U.S. Government may have certain rights in this invention pursuant to National Institutes of Standards and Technology (NIST) Contract No. 70NANB9H3038.

BACKGROUND OF THE INVENTION

The present invention relates generally to a method and an apparatus for characterizing the barrier properties of members of combinatorial libraries. More specifically, the present invention relates to a method and an apparatus for performing real-time measurements of the permeability of water vapor into an array of coating materials and coatings, the method and the apparatus utilizing an array of acoustic wave devices.

In the combinatorial discovery of coating materials, such as barrier coating materials, the rapid characterization of the barrier properties of the coating materials and the evaluation of the moisture permeability of the coating materials are of primary importance. The transport of vapors, such as analyte vapors and water vapor, in and through the coatings is typically measured by exposing one side of a given coating to an analyte vapor while nitrogen gas sweeps the other side of the coating and any analyte vapor present in the atmosphere to a detector. The detector measures the rate at which the analyte vapor permeates the coating. Another method measures the amount of an out-gassed vapor present when a coating is deposited onto a non-permeable substrate and exposed to a vapor of interest. These methods, although marginally effective, require the utilization of large areas of coating in order to obtain a measurable signal, provide low measurement sensitivity, and make it difficult to simultaneously characterize the barrier properties of a plurality of coatings, especially to moisture.

Thus, what is needed is a method and an associated apparatus that require the utilization of only small areas of coating in order to obtain a measurable signal, provide relatively high measurement sensitivity, and make it possible to simultaneously characterize the barrier properties of a plurality of coatings, especially to moisture.

BRIEF SUMMARY OF THE INVENTION

The present invention provides a method and an associated apparatus for the real-time characterization of the barrier properties of an array of coatings, the method and the apparatus utilizing an array of acoustic wave devices.

In one embodiment of the present invention, a method for characterizing the barrier properties of an array of coatings includes providing a plurality of acoustic wave devices, wherein each of the plurality of acoustic wave devices comprises at least one surface, and providing a plurality of coating materials suitable for forming a plurality of coatings on the at least one surface of each of the plurality of acoustic wave devices. The method also includes coating each of the plurality of acoustic wave devices with at least one of the plurality of coating materials to form a plurality of coated acoustic wave devices and measuring a predetermined output parameter of each of the plurality of coated acoustic wave devices. The method further includes exposing the plurality of coated acoustic wave devices to an analyte vapor of a predetermined concentration, measuring the predetermined output parameter of each of the plurality of coated acoustic wave devices, and correlating a change in the predetermined output parameter of each of the plurality of coated acoustic wave devices to a barrier property of interest or the moisture permeability of each of the plurality of coatings.

In another embodiment of the present invention, an apparatus for characterizing the barrier properties of an array of coatings includes a plurality of acoustic wave devices, wherein each of the plurality of acoustic wave devices comprises at least one surface, and wherein the plurality of acoustic wave devices are arranged in an array. The apparatus also includes a plurality of coating materials suitable for forming a plurality of coatings on the at least one surface of each of the plurality of acoustic wave devices. The apparatus further includes means for coating each of the plurality of acoustic wave devices with at least one of the plurality of coating materials to form a plurality of coated acoustic wave devices and an array of coatings, and a means for measuring a predetermined output parameter of each of the plurality of coated acoustic wave devices. The apparatus further includes means for exposing the plurality of coated acoustic wave devices to an analyte vapor of a predetermined concentration and a correlation factor operable for correlating a change in the predetermined output parameter of each of the plurality of coated acoustic wave devices to a barrier property of interest or moisture permeability of each of the plurality of coatings of the array of coatings.

DETAILED DESCRIPTION OF THE INVENTION

Figure 1:
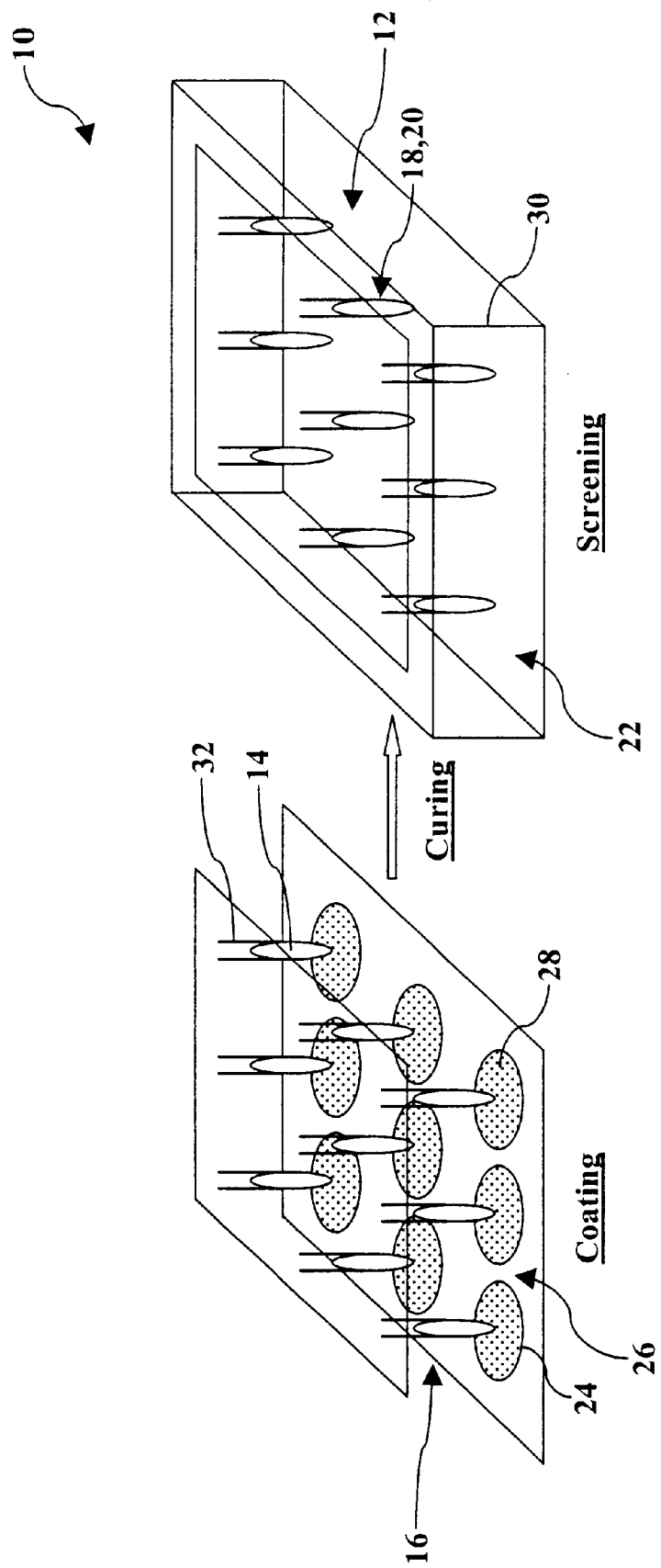
FIG. 1 is a schematic diagram of one embodiment of an apparatus for measuring a barrier property of an array of coatings.

Referring to FIG. 1, in one embodiment of the present invention, an apparatus 10 for the measurement of the moisture permeability of an array of coatings 12, such as an array of barrier coatings, includes a plurality of acoustic wave devices 14 arranged in an array 16. The acoustic wave devices 14 are useful for the quantitation of chemical species as the output parameters of each acoustic wave device 14 vary as a function of the mass of a coating 18 deposited onto a surface 20 of the acoustic wave device 14. The mass of the coating 18 deposited onto the surface 20 of each acoustic wave device 14, in turn, varies as a function of the analyte concentration in the coating 18, i.e. the amount of analyte vapor 22 that permeates the coating 18. Thus, the output parameters of each acoustic wave device 14 vary as a function of the analyte concentration in the coating 18 deposited onto the surface 20 of the acoustic wave device 14. These output parameters may include, for example, fundamental oscillation frequency, the velocity of an acoustic wave traveling through the coating, the attenuation of an acoustic wave traveling through the coating, capacitance change, and the like. Suitable acoustic wave devices 14 include thickness-shear mode (TSM) devices and the like. For example, suitable acoustic wave devices 14 include high (1 MHz–70 MHz) and low (100 Hz–1 MHz)-frequency TSM resonators, surface acoustic wave devices, Lamb wave (LW) devices, flexural plate wave devices, acoustic plate mode (APM) devices, Love wave devices, bimorphs, unimorphs, cantilevers, torsion resonators, tuning forks, membrane resonators, and the like. The plurality of acoustic wave devices 14 may also be utilized to measure changes in the viscoelastic properties of a coating 18. The plurality of acoustic wave devices 14 are preferably arranged in an array 16 such that a barrier property of interest or the moisture permeability of an array of coatings 12, including a plurality of individual or discrete coatings 18, may be measured simultaneously.

The apparatus 10 also includes a plurality of wells 24, arranged in an array 26, suitable for containing a plurality of individual or discrete coating materials 28. The apparatus 10 further includes a gas flow cell 30 suitable for containing a volume of analyte gas or vapor 22 of a predetermined concentration to which the array of coatings 12 may be exposed. The apparatus 10 may also be operatively connected to a plurality of TSM devices 14, via a plurality of leads 32, that measure the change in mass of each oscillating acoustic wave device 14, the change in the oscillation frequency of each acoustic wave device 14 associated with the permeation of water molecules, or the like, into the associated coating 18. The coating 18 may, optionally, be a multi-layer coating 18. Other suitable coating systems and deposition methods include, but are not limited to, spray nozzles or guns of any type (such as air, airless, thermal, ultrasonic, or hydraulic force spray nozzles or guns), casting heads, electron-beam evaporators, sputtering devices, chemical vapor deposition devices, ink jet print heads, draw-down devices, and linear coating heads.

As described above, an acoustic wave transducer includes a piezoelectric crystal which allows transduction between electrical and acoustic energies. These devices are known in a number of configurations to those of ordinary skill in the art. These configurations may be described based on their unique acoustic modes, such as thickness-shear mode (TSM), surface acoustic wave (SAW), acoustic plate mode (APM), flexural plate wave (FPW), and surface transverse wave (STW) devices. Non-piezoelectric acoustic wave devices may also be utilized. A thin-rod acoustic wave device is an example of a non-piezoelectric acoustic wave device. The thin-rod acoustic wave device may be operated at low frequencies (about 200 kHz). Other acoustic wave devices may also be made of non-piezoelectric materials. These devices include, for example, cantilevers, torsion resonators, tuning forks, bimorphs (i.e. a type of two-pronged tuning fork), unimorphs (i.e. a type of single-pronged tuning fork), membrane resonators, etc. Materials of construction may be glass, metals, etc.

The operating frequencies of suitable acoustic wave devices may be in the following ranges: thickness-shear mode (TSM), about 0.1-about 70 MHz; surface acoustic wave (SAW), about 30-about 10000 MHz; acoustic plate mode (APM), about 20-about 500 MHz; flexural plate wave (FPW), about 0.01-about 10 MHz; surface transverse wave (STW), about 100-about 1000 MHz; and thin-rod acoustic wave (TRAW), about 0.2-about 1 MHz. For non-piezoelectric acoustic wave devices, such as bimorphs, unimorphs, cantilevers, torsion resonators, tuning forks, membrane resonators, etc., the operating frequencies are in the range of about 1 Hz-about 1 MHz. In general, the acoustic wave device 14 of embodiments of the present invention operate in a frequency range of about 10 GHz-about 0.1 Hz, preferably in the range of about 500 MHz-about 1 kHz, and more preferably in the range of about 100 MHz-about 100 KHz.

The acoustic wave devices 14 are typically about 0.2 mm to about 50 mm in length, in cylindrical or rectangular shapes, and about 10 microns to about 2 mm in thickness, although other sizes and shapes may be utilized. Further, the minute quantity of material may deposited on the acoustic wave devices 14 may be in the range of about 1 picogram to about 1 milligram, preferably in the range of about 100 picograms to about 10 milligrams, and more preferably in the range of about 1 nanogram to about 1 microgram. The quantity of the material depends upon the operating frequency of the device 14 and its electronic circuitry.

The acoustic wave devices 14 may be one- or two-port devices. In one-port devices, such as TSM devices, a single port serves as both the input and the output port. The input signal excites an acoustic mode, which in turn generates charges on the input electrode. These signals combine to produce an impedance variation that constitutes the TSM resonator response. In two-port devices, one port is used as the input port and the other as an output port. The input signal generates an acoustic wave that propagates to a receiving transducer which generates a signal on the output port. The relative signal level and phase delay between input and output ports constitute two responses.

In a TSM device, an oscillating potential is applied to electrodes deposited onto two opposite sides of an acoustic wave material, such as a quartz crystal. This acoustic wave material oscillates in the thickness-shear mode with a fundamental frequency measured using a conventional frequency counter. Such an acoustic wave device allows measurement of such variations as the change in mass of a material or coating applied to the oscillating crystal, as well as several other properties of the material such as density, crystallinity, and viscosity, after accounting for other factors, such as the dimensions and other parameters of the crystal, as well as variables, such as the temperature at which measurement is made.

Substrate materials of acoustic wave transducers may include quartz, lithium niobate, nitride, lithium tantalate, bismuth germanium oxide, aluminum nitride, or gallium arsenide, and acoustic-wave films (ZnO and AlN). Non-piezoelectric materials are also used. Measurement of the acoustic-wave device properties is made using electronic equipment such as a network analyzer, a vector voltmeter, an impedance analyzer, frequency counter, a phase interferometer, and an in-phase and quadrature demodulator.

Figure 2:
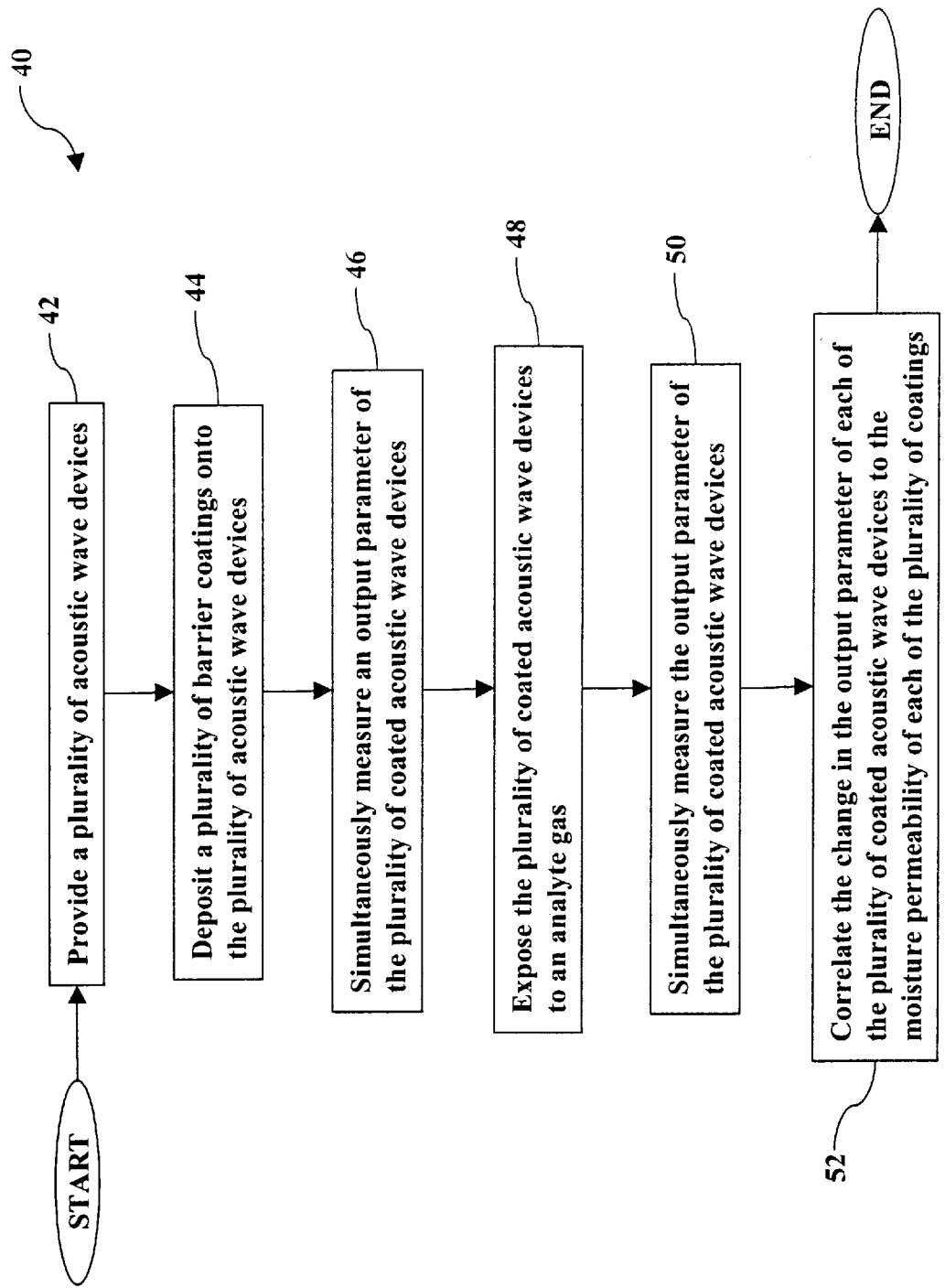
FIG. 2 is a flow chart of one embodiment of a method for measuring a barrier property of an array of coatings.

Referring to FIG. 2, in another embodiment of the present invention, a method 40 for the measurement of the moisture permeability of an array of coatings 12 (FIG. 1), such as an array of barrier coatings, includes providing a plurality of acoustic wave devices 14 (FIG. 1) (Block 42). As discussed above, suitable acoustic wave devices 14 include, for example, TSM devices and the like. The method 40 also includes depositing a plurality of coatings 18 (FIG. 1) onto a surface 20 (FIG. 1) of each of the plurality of acoustic wave devices 14 (Block 44) and simultaneously measuring an output parameter of each of the plurality of coated acoustic wave devices 14 (Block 46). This output parameter may include, for example, fundamental oscillation frequency, the velocity of an acoustic wave traveling through the coating, the attenuation of an acoustic wave traveling through the coating, impedance phase and magnitude, conductance, capacitance change, and the like. The plurality of coated acoustic wave devices 14 are then simultaneously exposed to an analyte gas or vapor 22 (FIG. 1) (Block 48). The analyte gas or vapor 22 may have a zero flow or a nonzero flow across elements of the coating array 12. The concentration of the analyte gas or vapor 22 may range from parts per billion to about 100 percent. The partial pressure of the analyte gas or vapor 22 may range from about 0.001 atmosphere to about 100 atmospheres. The output parameter of each of the plurality of coated acoustic wave devices 14 is then simultaneously measured again (Block 50). Measurements are performed periodically upon the exposure of the coating array 12 to analyte. Finally, the change in the output parameter of each of the plurality of coated acoustic wave devices 14 is correlated to a barrier property of interest or the moisture permeability of each of the plurality of coatings 18 (Block 52). This correlation may be performed utilizing, for example, a multivariate statistical analysis.

Figure 3:
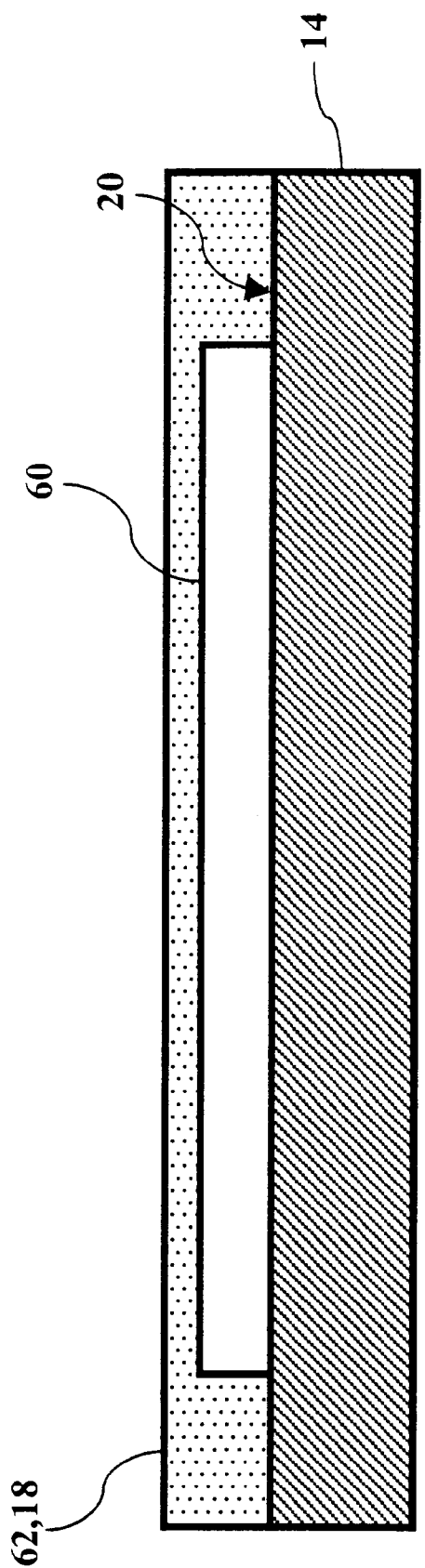
FIG. 3 is a schematic diagram of another embodiment of an apparatus for characterizing the barrier properties of an array of coatings.
Figure 4:
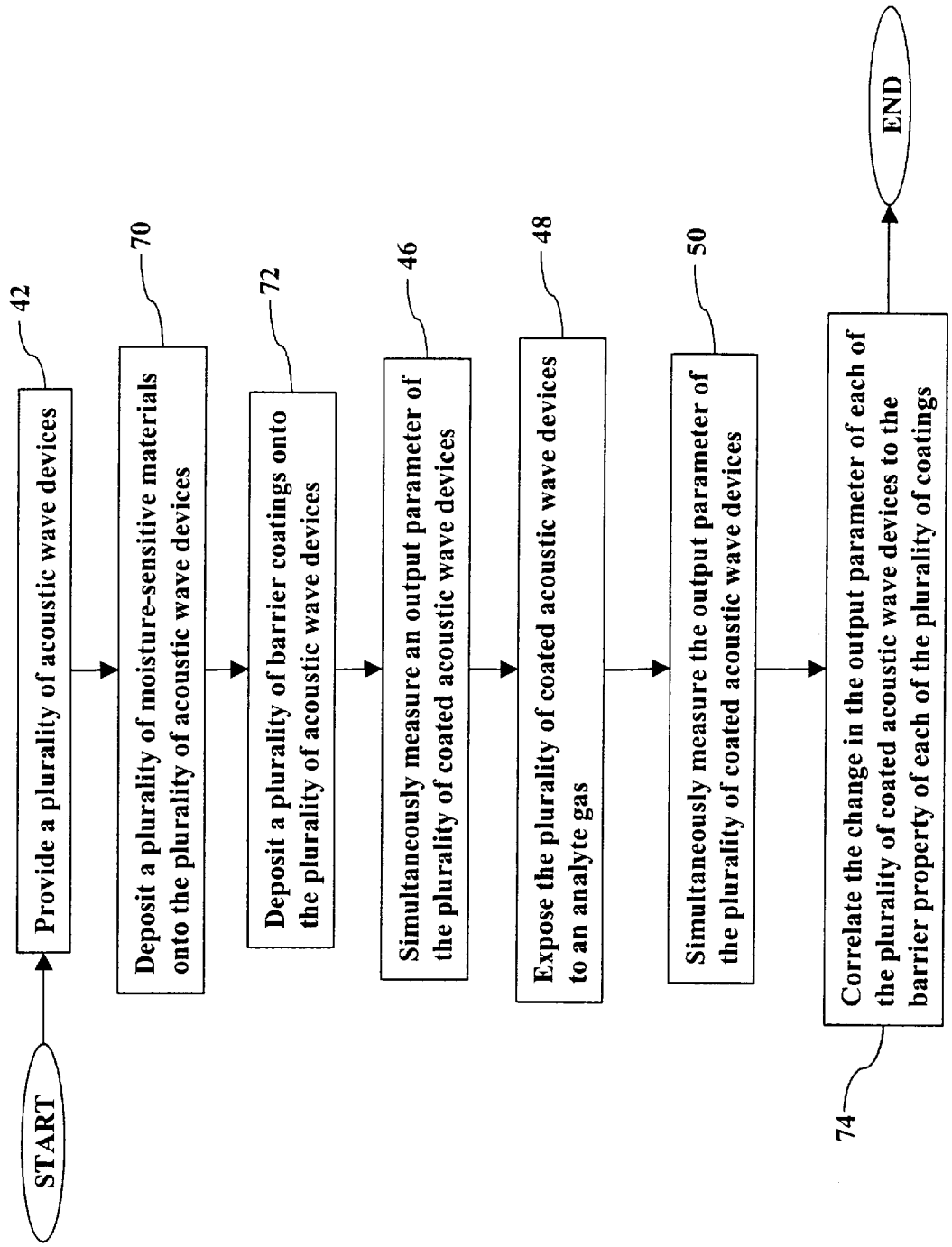
FIG. 4 is a flow chart of another embodiment of a method for characterizing the barrier properties of an array of coatings.

Referring to FIGS. 3 and 4, in a further embodiment of the present invention, a highly moisture-sensitive coating 60 is applied to the surface 20 of each of the plurality of acoustic wave devices 14 (Block 70). A film 62 having a barrier property of interest is applied on top of the moisture-sensitive coating 60 (Block 72). The change in the output parameter of each of the plurality of coated acoustic wave devices 14 is then simultaneously measured (Blocks 46 and 50). Finally, the change in the output parameter of each of the plurality of coated acoustic wave devices 14 is correlated to the barrier property of interest of each of the plurality of coatings 18 (Block 74).

In a further embodiment of the present invention, a substrate is applied to the surface 20 of each of the plurality of acoustic wave devices 14. A film having a barrier property of interest is applied on top of the substrate. The change in the output parameter of each of the plurality of coated acoustic wave devices 14 is then simultaneously measured. Finally, the change in the output parameter of each of the plurality of coated acoustic wave devices 14 is correlated to the barrier property of interest of each of the plurality of coatings 18.

Figure 5:
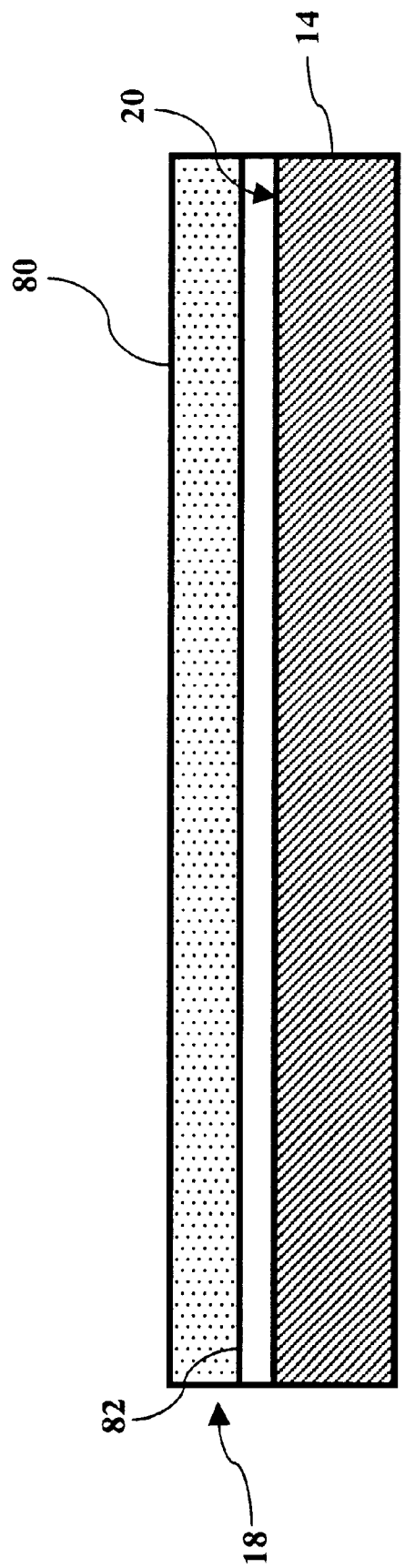
FIG. 5 is a schematic diagram of another embodiment of the apparatus for characterizing the barrier properties of an array of coatings.
Figure 6:
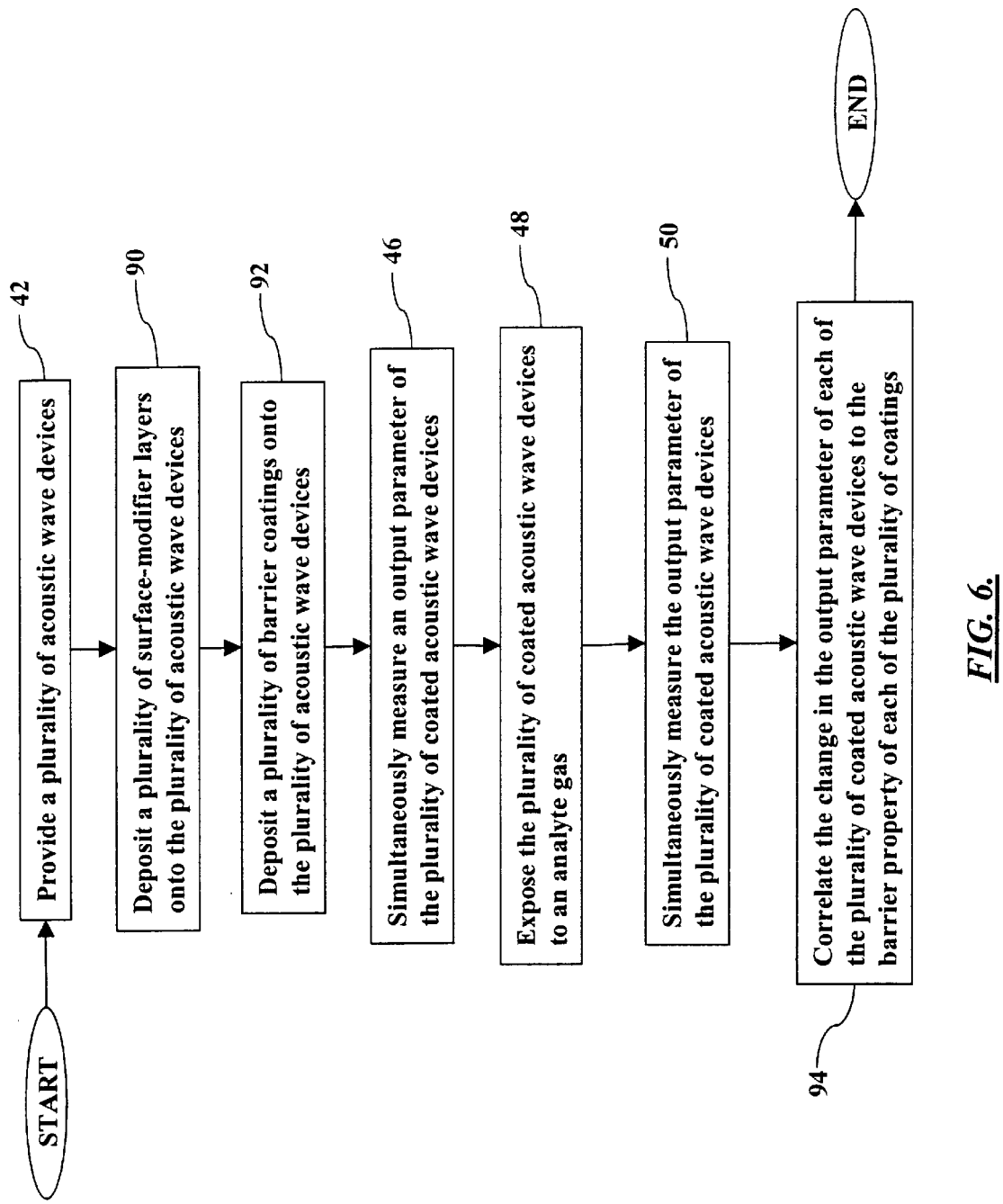
FIG. 6 is a flow chart of another embodiment of the method for characterizing the barrier properties of an array of coatings.

Referring to FIGS. 5 and 6, in a further embodiment of the present invention, the surface 20 of each of the plurality of acoustic wave devices 14 is modified to contain desired functional groups, and to have a predetermined surface energy suitable for the deposition of a barrier coating 80 in order to approximate the surface of a material to which the barrier coating 80 would be applied in a real-world application. This modification may be accomplished through the deposition or creation of a surface-modifier layer 82 (Block 90). A film 80 having a barrier property of interest is applied to the surface 20 of each of the plurality of acoustic wave devices 14 (Block 92). The change in the output parameter of each of the plurality of coated acoustic wave devices 14 is then simultaneously measured (Blocks 46 and 50). Finally, the change in the output parameter of each of the plurality of coated acoustic wave devices 14 is correlated to the barrier property of interest of each of the plurality of coatings 18 (Block 94).

Figure 7:
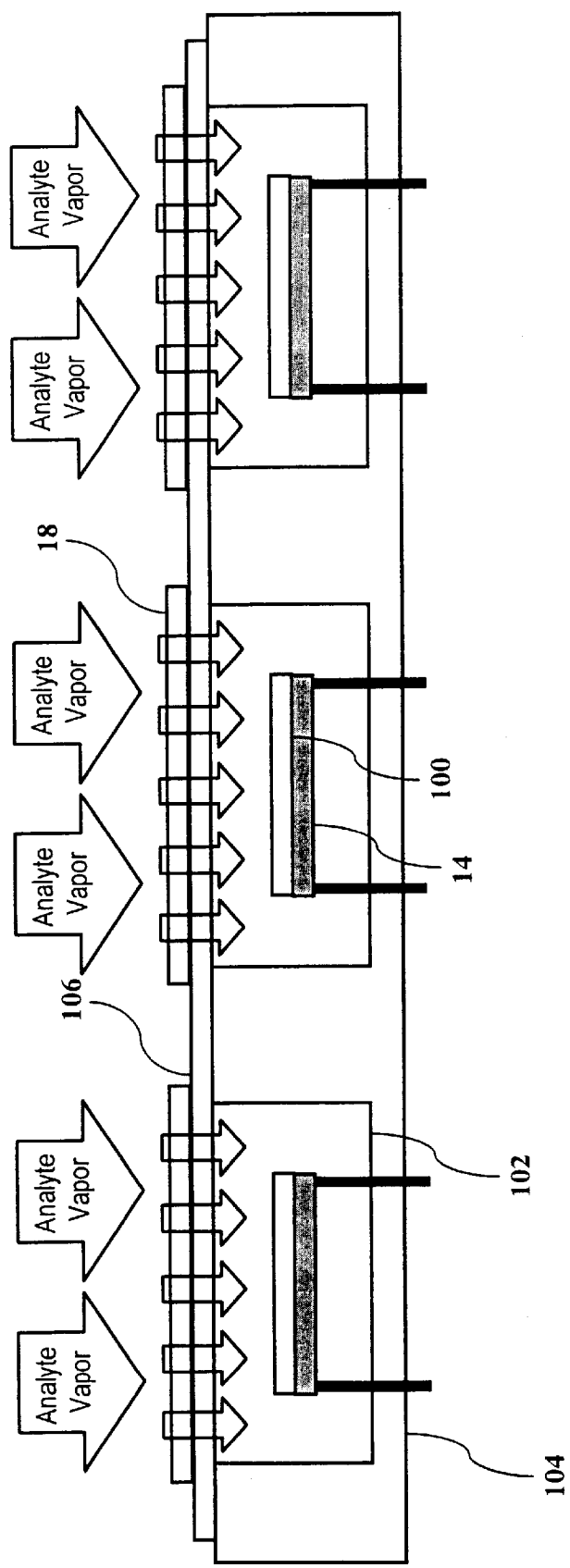
FIG. 7 is a schematic diagram of a further embodiment of the apparatus for characterizing the barrier properties of an array of coatings.
Figure 8:
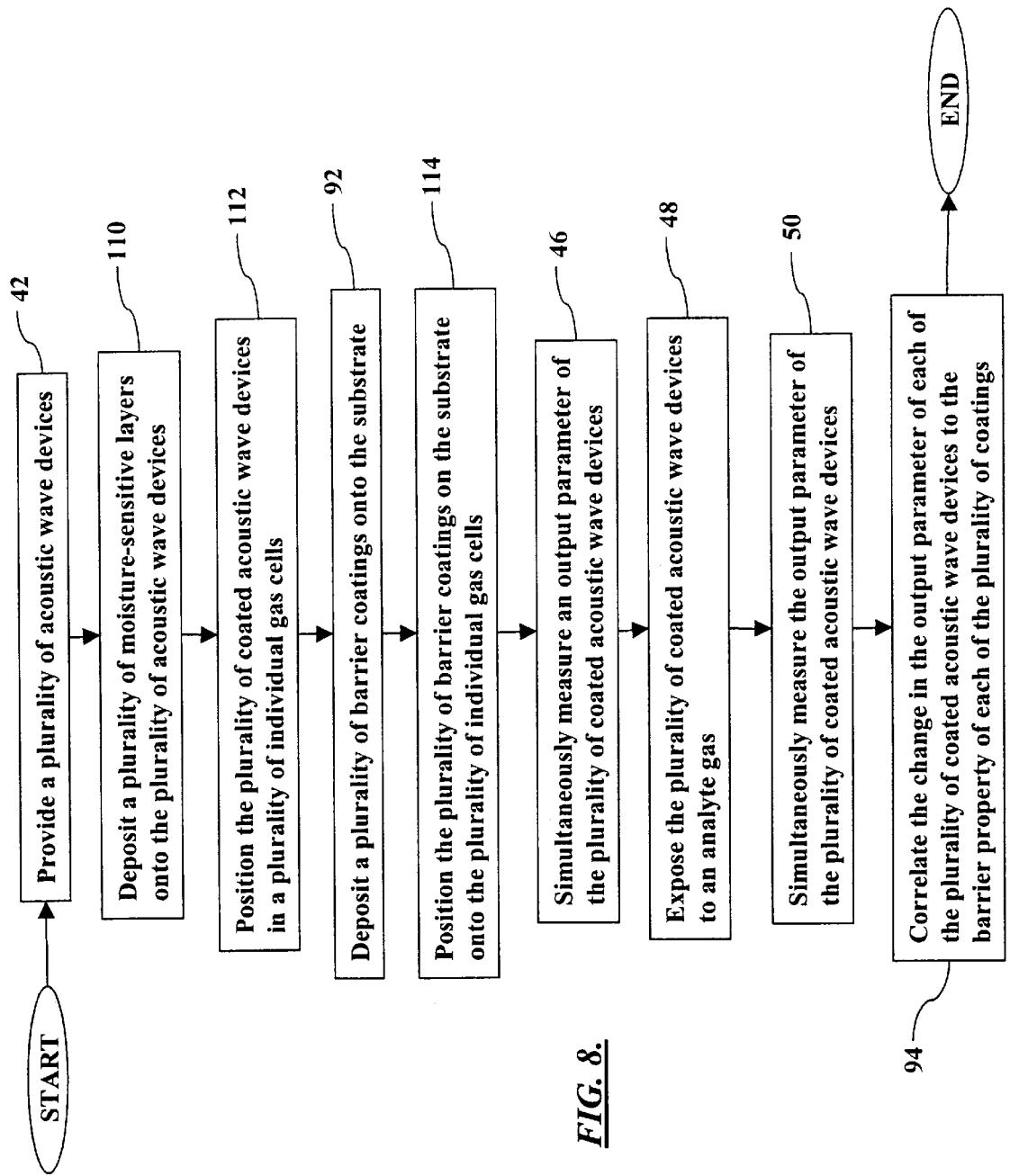
FIG. 8 is a flow chart of a further embodiment of the method for characterizing the barrier properties of an array of coatings.

Referring to FIGS. 7 and 8, in a still further embodiment of the present invention, a plurality of moisture-sensitive layers 100 are deposited on the plurality of acoustic wave devices 14 (Block 110). The plurality of acoustic wave devices 14 are then disposed in a plurality of individual gas cells 102, optionally having a common base 104 (Block 112). A plurality of barrier coatings 18 are then disposed onto a substrate 106 suspended adjacent to the plurality of acoustic wave devices 14 (Block 92). In other words, the plurality of barrier coatings 18 and the substrate 106 are positioned on the plurality of individual gas cells 102 (Block 114). The output parameter of each of the plurality of acoustic wave devices is then measured, as described above with reference to the other embodiments of the present invention.

In one embodiment of the present invention, the mathematical analysis performed involves multivariate analysis. Preferably, the multivariate analysis involves principal components analysis, neural networks analysis, partial least squares analysis, linear multivariate analysis, or nonlinear multivariate analysis.

The method and apparatus of the present invention apply mathematical analysis in order to improve the resolution of the acoustic wave sensors, thus reducing the time required to identify preferred barrier coating candidates. Preferred barrier coating candidates are coatings with the lowest relative moisture permeability or the highest relative barrier property to moisture. Thus, the mathematical analysis may involve multivariate analysis using multivariate measurement, wherein multivariate measurement includes measurements of more than one variable or response for each sample. For example, the velocity and the attenuation of an acoustic wave traveling through a deposited coating may be measured by a single acoustic wave transducer.

Suitable types of multivariate analysis include linear multivariate analysis, nonlinear multivariate analysis, partial least squares analysis, principal components analysis, and neural networks analysis. Generally, linear multivariate analysis is used to describe linear relationships between independent and dependent variables using straight line calibration functions, and non-linear multivariate analysis is used to describe nonlinear relationships between independent and dependent variables. Principal components analysis and factor analysis are transforms that find and interpret hidden complex and possibly causally determined relationships between features in a data set; the correlating features are then converted to factors which are themselves non-correlated. Partial least squares (PLS) analysis and principal components regression (PCR) analysis make use of an inverse calibration approach where it is possible to calibrate for the desired component(s) while implicitly modeling the other sources of variation; the difference between PLS and PCR is in how the factors are calculated. Neural networks analysis describes analysis of a data set to a specific problem by iterative adjustment of weights in a net during the learning process; this adaptation may be done either by comparison of the desired result with the data at the output of the net (supervised learning) or by maximizing differences in the learning data based on an arbitrary criterion of similarity (unsupervised learning). The multivariate analysis tools of the present invention improve the resolution of the acoustic wave sensors and thus reduce the time required to identify preferred barrier coating candidates. Preferred coating candidates are coatings with the lowest relative moisture permeability or the highest relative barrier property to moisture.

WORKING EXAMPLE

An apparatus for the simultaneous evaluation of the barrier properties of a plurality of coatings included different coating materials or formulations disposed within the wells of a standard microtiter plate. An array of TSM devices was immersed in the wells to dip coat the crystals of the TSM devices with the plurality of coating materials, forming a combinatorial library. The thickness of the liquid coating materials was varied by diluting the initial coating formulations and each of the plurality of coatings was cured at about 120 degrees C. for about 10–60 minutes. After curing, the array of TSM devices was exposed to nitrogen gas with a relative humidity alternating between about 0% and about 90%. Data analysis was performed taking into account the dynamics and the absolute value of the responses obtained. This approach allowed for the screening of the plurality of coatings for the lowest water transport properties.

During testing, the array of TSM devices was oscillated at about 10 MHz. Each TSM device was capable of detecting a mass change with a sensitivity of about 44 pg. The resolution of the frequency measurements was about 0.05 Hz. Results of this experiment demonstrated several important advantages of the method and apparatus of the present invention. Surface and bulk water sorption effects were discriminated as the measured TSM device signal increased directly as a function of coating thickness. Measurements obtained using the method and apparatus of the present invention were readily reproducible, providing a relative standard deviation of only about 1%. The diffusion rate for each coating was determined from the dynamic response of each coated TSM crystal upon a step change in gas/vapor composition. The TSM devices were free from contributions resulting from changes in the viscoelastic properties of the barrier coatings, providing accurate moisture permeability results. Finally, the measurement of the barrier properties of coatings deposited onto TSM devices provided simple miniaturization and multiplexing routines, making parallel moisture permeability measurements possible using only small areas of coating.

It is important to note that the moisture-sensitive coating or barrier coating may be applied to the acoustic wave devices using thin-film deposition techniques in combination with physical masking techniques or photolithographic techniques. Such thin-film deposition techniques may generally be broken down into the following four categories: evaporative methods, glow discharge processes, gas-phase chemical processes, and liquid-phase chemical techniques. Included within these categories are, for example, sputtering techniques, spraying techniques, laser ablation techniques, electron beam or thermal evaporation techniques, ion implantation or doping techniques, chemical vapor deposition techniques, as well as other techniques used in the fabrication of integrated circuits. All of these techniques may be applied to deposit highly uniform layers, i.e., thin-films, of the various materials of interest on selected regions on the device. Other types of coating procedures are also easily applicable in conjunction with the methods of the present invention to deposit the materials of interest. These other coating procedures may include, for example, spin-coating, brushing, and laser deposition. Conventional liquid-handling instruments (for example, the Quadra 96 Model 230 liquid delivery system available from Tomtec, Orange, Conn., and an eight-probe liquid handler system from Gilson) may be utilized to deposit solutions of coatings onto the individual transducers of an array of acoustic wave devices. When the transducer array and solvent well array have different layouts, a conventional liquid-handling instrument with variable spacing between the liquid-delivery tips (for example, Model Lissy from Zinsser Analytic of Frankfurt, Germany) is utilized to transfer solvents from the wells directly onto the array of crystals or into another array of wells.

In yet a further embodiment of the present invention, the delivery of solid components of coating formulations to the solvent-containing wells is accomplished using, for example, a conventional solid-handling instrument. Such an instrument is capable of delivering a predetermined amount of a solid material into each of the wells, previously filled with a solvent, or filled with a solvent after the delivery of a solid sample. Stirring, if needed, is provided using, for example, known stirring equipment for multiple wells (e.g., a heating/stirring module Reacti-Therm III available from Pierce of Rockford, Ill.). Other alternative methods for transferring a portion or all of the solvents or other chemicals in the wells to the acoustic wave devices are well known to those of ordinary skill in the art.

Optionally, the material or combination of materials may form a coating having a plurality of layers, where the coating may be a multi-functional coating having an overall function dictated by a predefined functional role of each layer. The plurality of materials may be combined such that multiple organic materials are combined into a coating. By providing these various combinations of the plurality of materials, the interaction and compatibility of various combinations may be determined through the use of the testing device. The coating is a material or a combination of materials deposited on the surface of the substrate. These materials may remain as separate homogenous materials, or they may interact, react, diffuse, mix, or otherwise combine to form a new homogeneous material, a mixture, a composite, or a blend. Each member of the array of coatings is distinguishable from the others based upon its location. Further, each member of the array of coatings may be processed under the same conditions and analyzed to determine its performance relative to functional or useful properties, and then compared with each of the other members of the array of coatings to determine its relative utility. Alternatively, each member of the array of coatings may be processed under different conditions and the processing methods may be analyzed to determine their performance relative to functional or useful properties, and then compared with each other to determine their relative utility.

The curing source is a device in communication with each of the plurality of materials causing a reaction or solvent evaporation with one or a combination of the plurality of materials. For example, the reaction may be a polymerization reaction, a cross-linking reaction, a small molecule reaction, an inorganic phase reaction, and other similar reactions appropriate for the delivered material(s). The curing source accomplishes this by delivering a curing medium. The curing medium may be any form of energy or suitable material that interacts with the combination of the plurality of materials forming the coating to sufficiently cure or condition the coating. Conditioning may include cross-linking, solvent evaporation, weathering, exposure to heat, UV-visible radiation, electromagnetic radiation, laser light, and the like. Suitable examples of curing environments preferably include those created by a curing source selected from the group consisting of ultraviolet (UV) radiation, infrared (IR) radiation, thermal radiation, microwave radiation, visible radiation, narrow-wavelength radiation, laser light, and humidity.

The barrier coating 18 may include any material for which a barrier property with respect to a given fluid is desired to be quantified. A suitable barrier coating may include, but is not limited to, any organic material, preferably polymers with additives, polycarbonates, polycarbonate blends, silicones, polycarbonate-polyorganosiloxane copolymers, polyetherimide resins, oxides, nitrides and oxinitrides of silicon, aluminum, zinc, boron and other metals, ceramics, polyvinyl alcohol, ethylene vinyl alcohol copolymers, polyvinyl dichloride, sol-gels, different types of nylon, cellophane, polyethylene terephtalate, PVC, PCTFE, polypropylene, and combinations thereof, as well as other similar materials typically used to provide a barrier to the transport of a given fluid. The barrier coating suitably has a thickness from about 0.1 nm to about 100 micrometers, preferably from about 1 nm to about 10 micrometers, and more preferably from about 10 nm to about 1 micrometer.

Suitable materials for the determination of moisture include a wide variety of gels, such as polyurethane gels, solid gels derived from polyacrylamide, polyvinyl pyrolidone, polyethylene oxide, or polyvinyl alcohol. Hygroscopic resins comprising a vinyl polymer are also acceptable. Illustrative polymers that may be used for moisture determinations using acoustic wave devices include the following: poly(ethylene oxide); polyvinyl pyrrolidone; polyacrylamide; anionic polyacrylamide; polyvinylalcohol; maleic anyhydride-vinylether copolymers; polyacrylic acid; ethylene-maleic anhydride copolymers; polyvinylethers; dextran; gelatin; hydroxy propyl cellulose; methyl cellulose; carboxymethyl cellulose; hydroxyethylcarboxymethyl cellulose; hydroxyethyl cellulose; propyleneglycol alginate; sodium alginate; polyethyleneimine; polyvinyl alkyl pyridinium halides, e.g. polyvinyl-n-butyl-pyridinium bromide; polyproline; natural starches; casein; proteins; polymethacrylic acid; polyvinylsulfonic acid; polystyrene sulfonic acid; polyvinylamine; ammonium polyacrylates; hydroxyalkyl acrylates; hydroxyalkyl methacrylates; hydroxyalkoxyalkyl acrylates; hydroxyalkoxyalkyl methacrylates; polyethylene oxide adduct esters of acrylic and methacrylic acids; alkoxy acrylates and methacrylates; alkoxyalkyl acrylates and methacrylates; partially hydrolyzed polyacrylamides; poly-4-vinylpyridine; polymerized monoesters of olefinic acids; polymerized diesters of olefinic acids; and acrylamide and difunctional polymerizable materials, e.g. diacids, diesters or diamides; and the like. These polymers may be cross-linked as required to have the desired degree of stability and the required amount of detector response. These materials may be prepared in a cross-linked state by a variety of techniques. Monomers may be polymerized with cross-linking agents, or the polymers may be cross-linked with condensation agents, such as di- or multivalent metal salts, or chemically, thermally, or by radiation-induced free radical reactions. Some uncross-linked polymers may also be used.

It is apparent that there have been provided, in accordance with the present invention, a method and an apparatus for characterizing the barrier properties of members of combinatorial libraries. While the present invention has been particularly shown and described in conjunction with examples and preferred embodiments thereof, it will be appreciated that variations in and modifications to the present invention may be effected by persons of ordinary skill in the art without departing from the spirit or scope of the invention. It is to be understood that the principles described herein apply in a similar manner, where applicable, to all such examples and embodiments and the following claims are intended to cover all such equivalents.

What is claimed is:

1. A high-throughput method for evaluating a barrier property of an array of coatings, the method comprising:
   providing a plurality of acoustic wave devices, wherein each of the plurality of acoustic wave devices comprises at least one surface;
   providing a plurality of coating materials suitable for forming a plurality of coatings on the at least one surface of each of the plurality of acoustic wave devices;
   coating each of the plurality of acoustic wave devices with at least one of the plurality of coating materials to form a plurality of coated acoustic wave devices;
   measuring a predetermined output parameter of each of the plurality of coated acoustic wave devices;
   exposing the plurality of coated acoustic wave devices to an analyte vapor of a predetermined concentration;
   measuring the predetermined output parameter of each of the plurality of coated acoustic wave devices; and
   correlating a change in the predetermined output parameter of each of the plurality of coated acoustic wave devices to the barrier property of each of the plurality of coatings.

2. The method of claim 1, further comprising curing the plurality of coatings.

3. The method of claim 1, wherein providing the plurality of acoustic wave devices comprises providing a plurality of acoustic wave devices selected from the group consisting of thickness-shear mode (TSM) devices, surface acoustic wave (SAW) devices, acoustic plate mode (APM) devices, flexural plate wave (FPW) devices, and surface transverse wave (STW) devices.

4. The method of claim 1, wherein providing the plurality of coating materials comprises providing a plurality of predetermined coating formulations.

5. The method of claim 1, wherein measuring the predetermined output parameter of each of the plurality of coated acoustic wave devices comprises measuring an oscillation frequency of each of the plurality of coated acoustic wave devices.

6. The method of claim 1, wherein measuring the predetermined output parameter of each of the plurality of coated acoustic wave devices comprises measuring an output parameter selected from the group consisting of the velocity of an acoustic wave traveling through each of the plurality of coatings, the attenuation of an acoustic wave traveling through each of the plurality of coatings, impedance phase and magnitude, conductance, and the capacitance change of each of the plurality of coatings.

7. The method of claim 1, wherein exposing the plurality of acoustic wave devices to the analyte vapor of a predetermined concentration comprises exposing the plurality of acoustic wave devices to water vapor of a predetermined concentration.

8. The method of claim 1, wherein measuring the predetermined output parameter of each of the plurality of coated acoustic wave devices comprises measuring the predetermined output parameter of each of the plurality of coated acoustic wave devices simultaneously.

9. The method of claim 1, wherein exposing the plurality of acoustic wave devices to the analyte vapor of a predetermined concentration comprises exposing the plurality of acoustic wave devices to the analyte vapor of a predetermined concentration simultaneously.

10. The method of claim 1, further comprising disposing a highly moisture-sensitive coating layer on the at least one surface of each of the plurality of acoustic wave devices.

11. The method of claim 1, further comprising modifying the at least one surface of each of the plurality of acoustic wave devices such that the at least one surface of each of the plurality of acoustic wave devices is suitable for deposition of the at least one of the plurality of coating materials.

12. The method of claim 1, further comprising identifying a coating of the array of coatings with a preferred barrier property utilizing a mathematical analysis tool.

13. The method of claim 12, wherein the mathematical analysis tool comprises a multivariate analysis tool.

14. The method of claim 13, wherein the multivariate analysis tool comprises a tool selected from the group consisting of principal components analysis, neural networks analysis, partial least squares analysis, linear multivariate analysis, and nonlinear multivariate analysis.

15. A high-throughput method for evaluating a barrier property of a plurality of coatings simultaneously, the method comprising:
providing a plurality of acoustic wave devices, wherein each of the plurality of acoustic wave devices comprises at least one surface;
providing a plurality of coating materials suitable for forming a plurality of coatings on the at least one surface of each of the plurality of acoustic wave devices;
coating each of the plurality of acoustic wave devices with at least one of the plurality of coating materials to form a plurality of coated acoustic wave devices;
conditioning the plurality of coatings;
measuring a predetermined output parameter of each of the plurality of coated acoustic wave devices simultaneously;
exposing the plurality of coated acoustic wave devices to an analyte vapor of a predetermined concentration, partial pressure, and temperature simultaneously;
measuring the predetermined output parameter of each of the plurality of coated acoustic wave devices simultaneously; and
correlating a change in the predetermined output parameter of each of the plurality of coated acoustic wave devices to the barrier property of each of the plurality of coatings.

16. The method of claim 15, wherein conditioning the plurality of coatings comprises a process selected from the group consisting of cross-linking, solvent evaporation, weathering, exposure to heat, UV-visible radiation, laser light, and electromagnetic radiation.

17. The method of claim 15, wherein providing the plurality of acoustic wave devices comprises providing a plurality of thickness-shear mode (TSM) devices.

18. The method of claim 15, wherein measuring the predetermined output parameter of each of the plurality of coated acoustic wave devices comprises measuring an oscillation frequency of each of the plurality of coated acoustic wave devices.

19. The method of claim 15, wherein measuring the predetermined output parameter of each of the plurality of coated acoustic wave devices comprises measuring an output parameter selected from the group consisting of the velocity of an acoustic wave traveling through each of the plurality of coatings, the attenuation of an acoustic wave traveling through each of the plurality of coatings, and the capacitance change of each of the plurality of coatings.

20. The method of claim 15, wherein exposing the plurality of acoustic wave devices to the analyte vapor of a predetermined concentration comprises exposing the plurality of acoustic wave devices to water vapor of a predetermined concentration.

21. The method of claim 15, further comprising depositing a moisture sensitive material on the at least one surface of each of the plurality of acoustic wave devices.

22. An apparatus for evaluating a barrier property of an array of coatings, the apparatus comprising:
a plurality of acoustic wave devices, wherein each of the plurality of acoustic wave devices comprises at least one surface, and wherein the plurality of acoustic wave devices are arranged in an array;
a plurality of coating materials suitable for forming a plurality of coatings on the at least one surface of each of the plurality of acoustic wave devices;
means for coating each of the plurality of acoustic wave devices with at least one of the plurality of coating materials to form a plurality of coated acoustic wave devices and the array of coatings;
means for measuring a predetermined output parameter of each of the plurality of coated acoustic wave devices;
means for exposing the plurality of coated acoustic wave devices to an analyte vapor of a predetermined concentration; and
a correlation factor operable for correlating a change in the predetermined output parameter of each of the plurality of coated acoustic wave devices to the barrier property of each of the plurality of coatings of the array of coatings.

23. The apparatus of claim 22, wherein the plurality of acoustic wave devices comprise a plurality of acoustic wave devices selected from the group consisting of thickness-shear mode (TSM) devices, surface acoustic wave (SAW) devices, acoustic plate mode (APM) devices, flexural plate wave (FPW) devices, and surface transverse wave (STW) devices.

24. The apparatus of claim 22, wherein the plurality of coating materials comprise a plurality of predetermined coating formulations.

25. The apparatus of claim 22, wherein the means for coating each of the plurality of acoustic wave devices with at least one of the plurality of coating materials comprise a plurality of wells suitable for containing the plurality of coating materials.

26. The apparatus of claim 22, further comprising a plurality of leads operable for coupling the means for measuring the predetermined output parameter of each of the plurality of coated acoustic wave devices to the plurality of acoustic wave devices.

27. The apparatus of claim 22, wherein the predetermined output parameter of each of the plurality of coated acoustic wave devices comprises an oscillation frequency of each of the plurality of coated acoustic wave devices.

28. The apparatus of claim 22, wherein the means for exposing the plurality of coated acoustic wave devices to an analyte vapor of a predetermined concentration comprise a gas flow cell suitable for containing the analyte vapor of a predetermined concentration.

29. The apparatus of claim 22, wherein the analyte vapor of a predetermined concentration comprises water vapor of a predetermined concentration.

30. The apparatus of claim 22, wherein the plurality of transducers are operable for measuring the predetermined output parameter of each of the plurality of coated acoustic wave devices simultaneously.

31. The apparatus of claim 22, wherein the means for exposing the plurality of coated acoustic wave devices to the analyte vapor of a predetermined concentration are operable for exposing the plurality of coated acoustic wave devices to the analyte vapor of a predetermined concentration simultaneously.

32. The apparatus of claim 22, wherein measuring the moisture permeability of an array of coatings comprises measuring the barrier properties of a plurality of coatings simultaneously.

33. The apparatus of claim 22, wherein the at least one surface of each of the plurality of acoustic wave devices has a surface energy and functional chemical groups suitable for deposition of the at least one of the plurality of coating materials.

34. The apparatus of claim 22, wherein materials for the determination of moisture comprise materials selected from the group consisting of gels, hygroscopic resins, polar polymers, and polymers with vinyl groups.

35. The apparatus of claim 22, wherein each of the plurality of acoustic wave devices is disposed in one of a plurality of individual gas cells and wherein each of the plurality of acoustic wave devices is positioned distal to each of the plurality of coatings.

36. An apparatus for evaluating a barrier property of a plurality of coatings simultaneously, the apparatus comprising:
   a plurality of acoustic wave devices, wherein each of the plurality of acoustic wave devices comprises at least one surface, and wherein the plurality of acoustic wave devices are arranged in an array;
   a plurality of coating materials suitable for forming a plurality of coatings on the at least one surface of each of the plurality of acoustic wave devices;
   a plurality of wells suitable for containing the plurality of coating materials, wherein the plurality of wells are operable for coating each of the plurality of acoustic wave devices with at least one of the plurality of coating materials to form a plurality of coated acoustic wave devices and the array of coatings;
   means for measuring a predetermined output parameter of each of the plurality of coated acoustic wave devices simultaneously;
   a gas flow cell suitable for containing an analyte vapor of a predetermined concentration, wherein the gas flow cell is operable for exposing the plurality of coated acoustic wave devices to the analyte vapor of a predetermined concentration simultaneously; and
   a correlation factor operable for correlating a change in the predetermined output parameter of each of the plurality of coated acoustic wave devices to the barrier property of each of the plurality of coatings of the array of coatings.

37. The apparatus of claim 36, wherein the plurality of acoustic wave devices comprise a plurality of non-piezoelectric acoustic wave devices selected from the group consisting of thin-rod acoustic wave (TRAW) devices, bimorph devices, unimorph devices, cantilevers, torsion resonators, tuning forks, and membrane resonators.

38. The apparatus of claim 36, further comprising a plurality of leads operable for coupling the means for measuring the predetermined output parameter of each of the plurality of coated acoustic wave devices to the plurality of acoustic wave devices.

39. The apparatus of claim 36, wherein the predetermined output parameter of each of the plurality of coated acoustic wave devices comprises an oscillation frequency of each of the plurality of coated acoustic wave devices.

40. The apparatus of claim 36, wherein the analyte vapor of a predetermined concentration comprises water vapor of a predetermined concentration.

41. The apparatus of claim 36, wherein each of the plurality of acoustic wave devices is disposed in one of a plurality of individual gas cells and wherein each of the plurality of acoustic wave devices is positioned distal to each of the plurality of coatings.

* * * * *